US011911476B2

(12) United States Patent
Pouletty et al.

(10) Patent No.: US 11,911,476 B2
(45) Date of Patent: Feb. 27, 2024

(54) PROCESS FOR PREPARING A DRUG DELIVERY COMPOSITION

(71) Applicant: PK MED SAS, Paris (FR)

(72) Inventors: Philippe Pouletty, Paris (FR); Frédérique Guillamot, Gerzat (FR)

(73) Assignee: PK MED, Paris (FR)

( * ) Notice: Subject to any disclaimer, the term of this patent is extended or adjusted under 35 U.S.C. 154(b) by 371 days.

(21) Appl. No.: 16/634,137

(22) PCT Filed: Jul. 25, 2018

(86) PCT No.: PCT/EP2018/070139
§ 371 (c)(1),
(2) Date: Jan. 25, 2020

(87) PCT Pub. No.: WO2019/020678
PCT Pub. Date: Jan. 31, 2019

(65) Prior Publication Data
US 2020/0368357 A1     Nov. 26, 2020

(30) Foreign Application Priority Data

Jul. 25, 2017 (EP) .................................. 17305993

(51) Int. Cl.
*A61K 47/34* (2017.01)
*B29C 48/00* (2019.01)
(Continued)

(52) U.S. Cl.
CPC ............ *A61K 47/34* (2013.01); *A61K 31/485* (2013.01); *A61K 38/47* (2013.01); *A61L 17/12* (2013.01);
(Continued)

(58) Field of Classification Search
CPC ..................................................... A61K 47/34
See application file for complete search history.

(56) References Cited

U.S. PATENT DOCUMENTS 10,626,242 B2   4/2020 Ferreira et al.
2008/0145403 A1*  6/2008 Spada .................. A61P 27/10
514/622

(Continued)

FOREIGN PATENT DOCUMENTS

WO   WO 03/094888    11/2003
WO   WO 2008/133724  11/2008
(Continued)

OTHER PUBLICATIONS

Ghalanbor, Z. et al. "Interdependency of protein-release completeness and polymer degradation in PLGA-based implants" *European Journal of Pharmaceutics and Biopharmaceutics*, 2013, pp. 624-630, vol. 85.

(Continued)

*Primary Examiner* — Carlos A Azpuru
(74) *Attorney, Agent, or Firm* — SALIWANCHIK, LLOYD & EISENSCHENK

(57) ABSTRACT

The present invention relates to process for preparing a drug delivery composition comprising the steps of a) preparing a masterbatch comprising a drug and a first polymer by (i) extruding the first polymer, wherein said first polymer has a melting temperature below 140° C.; and (ii) introducing the drug during extrusion of the first polymer, with a drug content between 0.1% and 90%, based on the total weight of the masterbatch; and b) introducing the masterbatch in a polymer-based matrix during production of the drug delivery composition, wherein step a) is performed at a temperature at which the first polymer is in a partially or totally molten state, and step b) is performed at a temperature at which both the first polymer and at least a polymer of the polymer-based matrix are in a partially or totally molten state.

23 Claims, 1 Drawing Sheet

(51) Int. Cl.
- *A61K 31/485* (2006.01)
- *A61K 38/47* (2006.01)
- *A61L 17/12* (2006.01)
- *A61L 24/00* (2006.01)
- *A61L 24/04* (2006.01)
- *A61L 27/18* (2006.01)
- *A61L 27/54* (2006.01)
- *A61L 31/06* (2006.01)
- *A61L 31/16* (2006.01)
- *C07K 16/24* (2006.01)
- *B29K 67/00* (2006.01)
- *B29K 105/00* (2006.01)

(52) U.S. Cl.
CPC ......... *A61L 24/0015* (2013.01); *A61L 24/046* (2013.01); *A61L 27/18* (2013.01); *A61L 27/54* (2013.01); *A61L 31/06* (2013.01); *A61L 31/16* (2013.01); *B29C 48/022* (2019.02); *C07K 16/241* (2013.01); *A61L 2300/216* (2013.01); *A61L 2300/254* (2013.01); *B29K 2067/043* (2013.01); *B29K 2067/046* (2013.01); *B29K 2105/0035* (2013.01); *B29K 2105/0085* (2013.01)

(56) References Cited

U.S. PATENT DOCUMENTS

| | | |
|---|---|---|
| 2014/0303278 A1 | 10/2014 | Ferreira et al. |
| 2016/0280881 A1 | 9/2016 | Boisart et al. |
| 2016/0333147 A1 | 11/2016 | Ferreira et al. |
| 2020/0206354 A1* | 7/2020 | Pouletty ............... A61K 9/2095 |

FOREIGN PATENT DOCUMENTS

| | | |
|---|---|---|
| WO | WO 2009/137673 | 11/2009 |
| WO | WO 2014/075185 | 5/2014 |
| WO | 201501020 A1 * | 4/2015 |
| WO | 2015051020 A1 * | 4/2015 |
| WO | WO 2015/051020 | 4/2015 |
| WO | WO 2016/019777 | 2/2016 |
| WO | WO 2016/198650 | 12/2016 |
| WO | WO 2017/081692 | 5/2017 |
| WO | WO 2019/020679 | 1/2019 |

OTHER PUBLICATIONS

Written Opinion in International Application No. PCT/EP2018/070139, dated Oct. 2, 2018, pp. 1-8.

* cited by examiner

PROCESS FOR PREPARING A DRUG DELIVERY COMPOSITION

CROSS-REFERENCE TO RELATED APPLICATION

This application is the U.S. national stage application of International Patent Application No. PCT/EP2018/070139, filed Jul. 25, 2018.

FIELD OF THE INVENTION

The present invention relates to a process for preparing a drug delivery composition comprising at least one drug included, and preferably embedded, in a polymer-based matrix. More particularly, the present invention relates to the use of a masterbatch containing a high amount of drug for preparing a drug delivery composition comprising a control amount of drug. The present invention also relates to a drug delivery device, preferably a medical device made with, or shaped from, said drug delivery composition.

BACKGROUND OF THE INVENTION

Delivery compositions for drugs are well known in the medical field. Among them, drug delivery devices have been developed that allow to release, with a more or less control rate, a drug in vivo. Most often, the drug is associated to a polymer, used as a vehicle for the drug. For instance, there are delivery devices composed of biodegradable polymers, wherein the drug is coated on the outer surface of the polymeric structure. Alternatively, some delivery devices are constituted of a polymeric structure, in which a drug is incorporated by use of a solvent. The use of a solvent is limited to incorporation of drug soluble in a solvent able to solubilize the polymer. For instance, drugs only soluble in water cannot be incorporated in non hydrosoluble polymers, such as the ones used for applications where specific mechanical properties are needed such as for suture, tissue engineering scaffold, etc. The amount of drug incorporated is also limited to solubility threshold. Moreover, small number of solvents are usable in medical field. Furthermore, the process of production using solvent is low and quality critical. Indeed, such production process includes steps of drying of the solvent, and cleaning of the composition in order to ensure the total absence of any trace of solvent in the final device. Production are also generally realized in batch, each of them requiring a stringent quality control. Some other drug delivery devices are constituted of a polymeric structure comprising pores filled with a liquid permeable to the passage of the drug. However, the use of a porous polymer does not lead to a homogenous reparation, or content uniformity, of the drug into the polymeric structure. The use of solid drug is excluded with these devices, which further require a liquid medium or carrier for the diffusion of the drug.

It is also known to disperse a drug into a polymer structure by the way of hot melt extrusion. The hot melt extrusion allows to prepare a large variety of dosage forms and formulations, such as granules, pellets, tablets, ophthalmic inserts, implants, stents or transdermal systems. This shows several advantages compared to solvent-based production processes, including continuous process and the absence of use of solvent which would have to be removed using costly and time-consuming steps. However, hot melt extrusion involves heat treatment that may impact the activity of the drug. And, the temperature at which a drug is at least partially inactivated may vary depending on the nature of the drug and/or the conditions of extrusion. Furthermore, up to now, only small drugs can be dispersed by hot melt extrusion, such as oligopeptides (e.g. goserilin acetate 1269 g/mol, melanotan 1024 g/mol). Indeed, thermal processes are not suitable for thermosensitive drugs such as proteins (Maniruzzaman et al., 2012 "A review of hot-melt extrusion: process technology to pharmaceutical products"; Stankovic et al., 2014 "Innovative platform technologies for stabilization and controlled release of proteins from polymer depots"). In addition, an accurate drug dosage may be hardly achieved by hot melt extrusion when low quantity of drugs must be introduced.

Accordingly, there is still a need for a process for preparing a drug delivery composition that leads both to a control dosage of the drug and to a homogeneous reparation of the drug into the whole polymer structure, without impairing on the activity of the drug into the composition and applicable to all drugs whatever their solubility, size and thermosensitivity.

SUMMARY OF THE INVENTION

Figure 1:
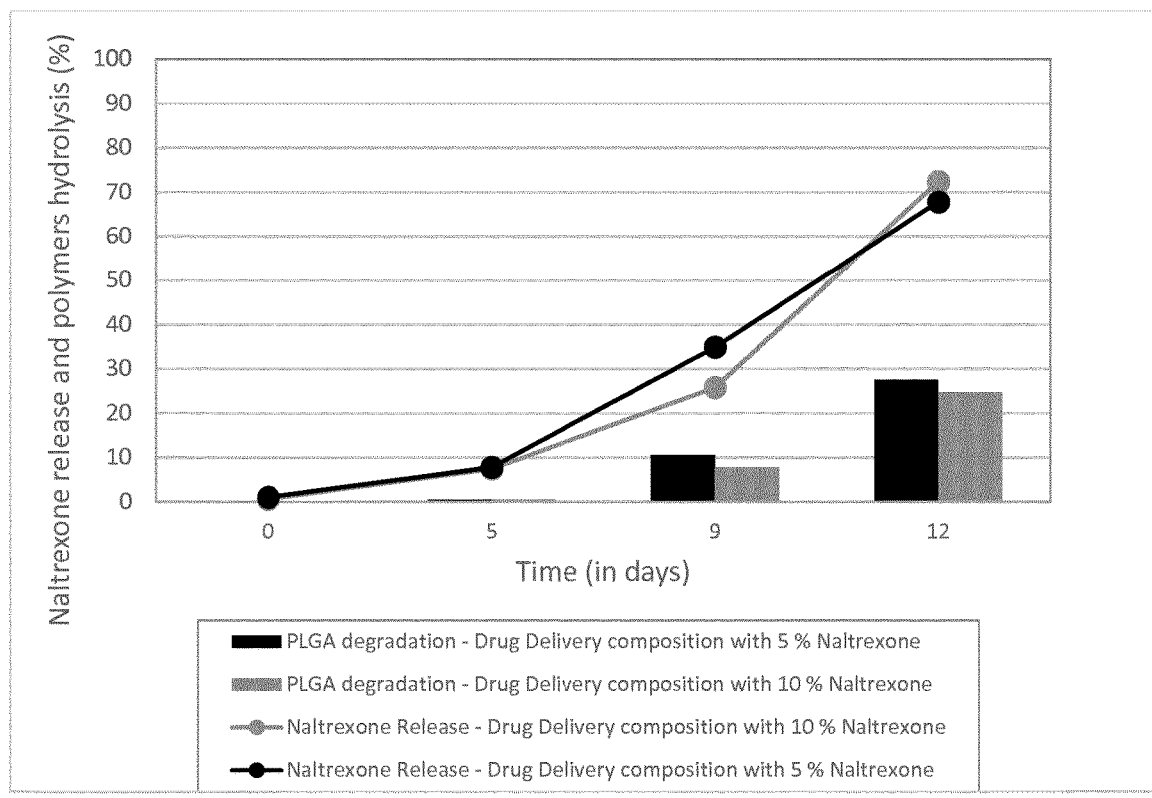
FIG. 1: PLGA degradation and naltrexone release of a drug delivery composition produced by the process of the invention comprising PLGA and 5% or 10% naltrexone.

The present invention now proposes a process for preparing a drug delivery composition comprising a drug homogeneously embedded into a polymer-based matrix. The process of the invention further allows to preserve an activity of the drug into the polymer-based matrix of the drug delivery composition. More particularly, the inventors have shown that high amounts of drugs (i.e., higher amount than the final dose required in the drug delivery composition) may be introduced into a first polymer, even during a mixing step performed at elevated temperature, preferably up to 140° C., and that the drugs in the resulting masterbatch retain an activity allowing the efficient production of drug delivery compositions, such as drug-delivery devices. The inventors have further shown that such masterbatch can advantageously be subsequently mixed with a polymer-based matrix during a mixing step performed at a higher temperature and that the drugs in the resulting composition retain an activity. In a particular embodiment, the invention proposes to introduce the masterbatch, and thereby the drug, at a late stage into the polymer-based matrix, to limit the residence time of the drug into a hot melted polymer-based matrix. The process of the invention is of particular interest for preparing a drug delivery device containing a thermosensitive or slightly solvent-soluble drug. The process of the invention is also of particular interest for preparing a drug delivery device containing a drug with a high molecular mass. Indeed, whereas molecules with high molecular mass are more heat sensitive than molecules with low molecular mass, the inventors have shown that the process of the invention allows to maintain an activity of drugs with high molecular mass, such as above 15 kDa, into a drug delivery device prepared with the process of the invention. Furthermore, the use of a masterbatch according to the process of the invention allows the production of drug delivery compositions with an improved dispersion and distribution rate of the drug in the device, thus leading to an improved control of the release. Thanks to the process, the release of the drug may be correlated with the degradation of the polymer. The use of a masterbatch and its dilution into the polymer-based matrix also allows to control with greater accuracy the drug content in the final drug delivery composition, even at very low concentration. In addition, thanks to the process, it is possible to significantly increase the drug content in the drug delivery composition as compared to the drug content in actual drug delivery composition. It is thus possible to prepare a drug feeder with the drug delivery composition of the invention, for long term applications.

It is thereby an object of the present invention to provide a process for preparing a drug delivery composition comprising at least a drug comprising the steps of
a) preparing a masterbatch comprising a drug and a first polymer by
(i) heating the first polymer, wherein said first polymer has a melting temperature below 140° C.; and
(ii) introducing the drug during heating of the first polymer, with a drug content between 0.1% and 90%, based on the total weight of the masterbatch; and
b) introducing the masterbatch in a polymer-based matrix during production of the drug delivery composition, wherein step a) is performed at a temperature at which the first polymer is in a partially or totally molten state, preferably by extrusion and step b) is performed at a temperature at which both the first polymer and at least a polymer of the polymer-based matrix are in a partially or totally molten state. Step a) is preferably performed at a temperature below 140° C.

In a particular embodiment, the drug has a molecular mass above 10 kDa, preferably above 14 kDa. In a preferred embodiment, the drug has a molecular mass and more preferably above 15 kDa.

It is another object of the invention to provide a drug delivery composition, obtainable by said process, wherein said composition comprises a drug included, and preferably embedded into a polymer-based matrix.

It is a further object of the invention to provide a drug delivery device, such as a medical device, shaped from, or made with, a drug delivery composition of the invention.

It is another object of the present invention to provide a process for preparing a drug delivery composition comprising at least a drug, comprising the step of introducing a masterbatch comprising a drug and a first polymer in a polymer-based matrix during production of the drug delivery composition, wherein the masterbatch is obtainable, or has been obtained, by heating the first polymer at a temperature at which the first polymer is in a partially or totally molten state, preferably below 140° C., and wherein the step of introducing the masterbatch in the polymer-based matrix is performed at a temperature at which both the first polymer and at least a polymer of the polymer-based matrix are in a partially or totally molten state.

According to an embodiment, the masterbatch comprises between 0.1% and 90% of drug, based on the total weight of the masterbatch.

Preferably, the first polymer has a melting temperature below 140° C.

It is another object of the present invention to provide a process for preparing a masterbatch comprising a drug and a polymer by
(i) heating the polymer, wherein said polymer has a melting temperature below 140° C.; and
(ii) introducing the drug during heating of the polymer, with a drug content between 0.1% and 90%, based on the total weight of the masterbatch;
wherein steps (i) and (ii) are performed at a temperature at which the polymer is in a partially or totally molten state, preferably below 140° C., preferably by extrusion.

Such masterbatch may then be used for preparing a drug delivery composition, by introducing said masterbatch in a polymer-based matrix.

DETAILED DESCRIPTION OF THE INVENTION

The present invention relates to a novel process for preparing a drug delivery composition composed of a polymer-based matrix, wherein at least a drug is incorporated. The process of the invention involves the use of a masterbatch comprising a first polymer and a high concentration of the drug, which is further diluted into a polymer-based matrix to form a drug delivery composition. The drug delivery composition of the invention shows both a controlled amount of drug and a good dispersion of the drug into the polymer-based matrix.

Definitions

The present disclosure will be best understood by reference to the following definitions.

Within the context of the invention, the term "drug delivery composition" refers to any composition, in liquid, gel or solid form, comprising at least one polymer-based material, which contains at least one polymer and at least one drug to be released from the composition.

Within the context of the invention, the term "drug delivery device" refers to any item made from at least one polymer-based material, preferably in solid form, such as plastic sheet, tube, rod, profile, shape, pellet, massive block, textile, fiber, scaffold, etc., which contains at least one polymer and at least one drug to be released. More preferably, the drug delivery device is a medical device.

As used herein, the term "masterbatch" designates a concentrated mixture of selected ingredients (i.e., drug) and polymer, which can be used for introducing said ingredients into plastic composition (i.e., drug delivery composition) in order to impart desired properties thereto. Masterbatch allows the processor to introduce selected ingredients economically during composition manufacturing process. Advantageously, the masterbatch is composed of a polymer wherein the selected ingredients are incorporated in high concentration. Generally, the masterbatch is mixed with a polymer to produce a final composition having a desired amount of selected ingredients. Preferably, the polymer of the masterbatch is compatible with the polymer of the final plastic composition that will incorporate the masterbatch. The masterbatch may further comprise mineral or organic fillers.

A "polymer" refers to a chemical compound or mixture of compounds, whose structure is constituted of multiple repeating units linked by covalent chemical bonds. Within the context of the invention, the term polymer includes natural or synthetic polymers, constituted of a single type of repeat unit (i.e., homopolymers) or of a mixture of different repeat units (i.e., copolymers). Within the context of the invention, the term polymer preferably refers to thermoplastic polymer.

A "polymer-based matrix" refers to a matrix comprising, as the main ingredient, one or more polymer(s). The polymer-based matrix comprises at least 51% by weight of polymer(s), based on the total weight of the composition, preferably at least 60%, 70%, 80%, 90% or 95%. The polymer-based matrix may further comprise additional compounds, such as additives. In a particular embodiment, the polymer-based matrix comprises at least 96%, 97%, 98%, or 99% by weight of polymer, based on the total weight of the composition.

A "drug" refers to any substance that is biologically active, i.e., that may have an impact on a living organism, including mammal, avian, virus, fungi and microorganisms. Notably, the term drug encompasses active substances, mineral or organic, that may have a prophylactic or therapeutic activity on a mammal, substances with antifungal and/or antimicrobial activity, etc. For instance, the drug is an active agent, such as pharmaceutical agent, Traditional Chinese Medicine, antibiotic, anti-cancer agent, anti-viral agent, anti-inflammatory agent, hormone, growth factor, etc., an antigen, a vaccine, an adjuvant, etc. The drug may also consist on a cosmetic agent. As used herein, the term "by weight" refers to the ratio based on the total weight of the considered composition or product.

In the context of the invention, the term "about" refers to a margin of +/−5%, preferably of +/−1%, or within the tolerance of a suitable measuring device or instrument.

Preparation of the Masterbatch

It is the purpose of the present invention to provide a process, wherein a masterbatch is prepared by (i) heating a first polymer, wherein said first polymer has a melting temperature below 140° C. and (ii) introducing the drug during heating of the first polymer, before to introduce said masterbatch into a polymer-based matrix in order to prepare the drug delivery composition, and in a particular embodiment in order to shape a drug delivery device.

According to the invention, the first polymer is heated at a temperature below 140° C., and the drug is introduced into the first polymer during said heating step. More generally speaking, the step of preparation of the masterbatch (step a) is performed at a temperature at which the first polymer is in a partially or totally molten state, so that the drug is embedded into the first polymer during the extrusion. With regard to amorphous polymers, a totally or partially molten state corresponds to a rubbery or softened state, i.e. a state at which such polymers are fluid enough to be processed by extrusion. Preferably, step a) is performed by extrusion. Alternatively, step a) is performed by internal mixing or co-kneading.

In preferred embodiment, the masterbatch is prepared by (i) extruding a first polymer, wherein said first polymer has a melting temperature below 140° C. and (ii) introducing the drug during extrusion of the first polymer, before to introduce said masterbatch into a polymer-based matrix in order to prepare the drug delivery composition. According to the invention, step a) is thus performed at a temperature below 140° C.

In a particular embodiment, the first polymer is a polyester and/or polyether, preferably selected from polycaprolactone (PCL), poly butylene succinate adipate (PBSA), polybutylene adipate terephthalate (PBAT), polydioxanone (PDS), polyhydroxyalkanoate (PHA), polylactic acid (PLA), polyglycolic acid (PGA), polyethylene glycol (PEG), preferably PEG with molecular mass above 600 g/mol, polyethylene oxide (PEO) or copolymers thereof.

In a preferred embodiment, the first polymer is a polyester, preferably selected from polycaprolactone (PCL), poly butylene succinate adipate (PBSA), polybutylene adipate terephthalate (PBAT), polyhydroxyalkanoate (PHA), polylactic acid (PLA), polyglycolic acid (PGA), or copolymers thereof. In a particular embodiment, the first polymer is a copolymer of polylactic acid and polyglycolic acid (PLGA or PLA-co-PGA). In another particular embodiment, the first polymer is PCL.

In a particular embodiment, the masterbatch comprises a "universal" polymer, i.e., a polymer that is compatible with a broad range of polymers, such as a copolymer (e.g. ethylene vinyl acetate copolymer EVA).

In a particular embodiment, the masterbatch comprises a first polymer that has a melting temperature below 140° C. and/or a glass transition temperature below 70° C. Preferably, the first polymer of the masterbatch has a melting temperature below 120° C., and/or a glass transition temperature below 30° C. For instance, such first polymer is selected from the group consisting of PCL and EVA. The advantage of such embodiment is to reduce the heating of the drug during the masterbatch production process.

In particular embodiment, the masterbatch is prepared by (i) extruding a first polymer selected from PCL, PLA or PLGA at a temperature below 140° C. and (ii) introducing the drug during extrusion of the first polymer. In a preferred embodiment, the first polymer is PCL and the extrusion is performed at a temperature between 55° C. and 80° C. In another preferred embodiment, the first polymer is PLGA and the extrusion is performed at a temperature between 80° C. and 100° C.

The masterbatch of the present invention comprises a drug content of between 0.1% and 90% by weight, based on the total weight of the masterbatch. Preferably, the drug represents between 0.1% and 80%, more preferably between 0.1% and 70%, even more preferably between 0.1% and 60% by weight, based on the total weight of the masterbatch.

Advantageously, the drug is chosen among molecules that have a molecular mass above 10 kDa, preferably above 14 kDa, more preferably above 15 kDa.

In a particular embodiment, the drug is deprived of any polymer-degrading activity.

According to the invention, the drug included into the masterbatch and thereby into the final drug delivery composition is chosen to act on a biological target. In the context of the invention, a "biological target" refers to any biological entity that may be directly or indirectly impacted by the drug. The biological target may be a whole body, an organ, a tissue, specific cells, etc., of an animal, such as a mammal or an avian, a microorganism, a virus, etc.

Preferably, the drug is selected from chemicals, pharmaceutical compound, nutraceutical compound, amino acids, peptides, proteins, polysaccharides, lipid derivatives, antibiotics, analgesics, vaccines, vaccine adjuvants, anti-inflammatory agents, anti-tumor agents, hormones, cytokines, antifungal agents, anti-viral agents, anti-bacterial agents, antidiabetics, steroids, vitamins, pro-vitamins, antioxidants, mineral salts, trace elements, specific enzyme inhibitor, growth stimulating agent, immunosuppressors, immunomodulators, anti-hypertensive drugs, anti-arrhythmic drugs, inotropic drugs, addiction therapy drugs, anti-epileptic drugs, anti-aging drugs, drugs to treat neuropathies or pain, hypolipemic drugs, anti-coagulants, antibodies or antibody fragments, antigens, anti-depressant or psychotropic agents, neuro-modulators, drugs for treating a disease selected from brain disease, liver disease, pulmonary disease, cardiac disease, gastric disease, intestine disease, ovary disease, testis disease, urological disease, genital disease, bone disease, muscle disease, endometrial disease, pancreatic disease and/or renal disease, ophthalmic drugs, anti-allergic agents, contraceptive or luteinizing agents, enzymes, Traditional Chinese Medicines, nutrients, cosmetics and mixtures of at least two of these drugs.

In a particular embodiment, the drug is selected from chemicals, pharmaceutical compound, amino acids, peptides, proteins, antibiotics, analgesics, vaccines, vaccine adjuvants, anti-inflammatory agents, anti-tumor agents, hormones, cytokines, anti-fungal agents, anti-viral agents, anti-bacterial agents, anti-diabetics, steroids, specific enzyme inhibitor, growth stimulating agent, immunosuppressors, immuno-modulators, anti-hypertensive drugs, anti-arrhythmic drugs, inotropic drugs, addiction therapy drugs, anti-epileptic drugs, anti-aging drugs, drugs to treat neuropathies or pain, hypolipemic drugs, anti-coagulants, antibodies or antibody fragments, antigens, anti-depressant or psychotropic agents, neuro-modulators, drugs for treating a disease selected from brain disease, liver disease, pulmonary disease, cardiac disease, gastric disease, intestine disease, ovary disease, testis disease, urological disease, genital disease, bone disease, muscle disease, endometrial disease, pancreatic disease and/or renal disease, ophthalmic drugs, anti-allergic agents, contraceptive or luteinizing agents, enzymes and mixtures of at least two of these drugs.

In a particular embodiment, the drug is chosen among compounds having therapeutic or prophylactic purposes in a mammal, and more particularly in a human.

In a particular embodiment, the drug is chosen from a protein having a molecular mass above 10 kDa such as lysozyme. In another particular embodiment, the drug is chosen from a protein having a molecular mass above 50 kDa, preferably above 100 kDa such as antibodies. In another particular embodiment, the drug is chosen from an enzyme having a molecular mass above 30 kDa, preferably above 50 kDa. In another particular embodiment, the drug is chosen from a hormone having a molecular mass above 9 kDa such as insulin or parathyroid hormone. In another particular embodiment, the drug is a growth hormone having a molecular mass above 20 kDa. In another particular embodiment, the drug is a hormone having a molecular mass above 30 kDa such as erythropoietin.

In a particular embodiment, the drug is chosen from antibodies, particularly from monoclonal antibodies. In another particular embodiment, the drug is chosen from a protein such as lysozyme. In another particular embodiment, the drug is chosen from a pharmaceutical compound used to manage alcohol or opioid dependence such as naltrexone.

In a particular embodiment, the drug is chosen among compounds having a denaturation temperature below 140° C., preferably below 100° C. The denaturation temperature corresponds to the temperature at which half of the drug loses its activity. Generally, the denaturation temperature is preferably above 50° C.

The present invention interestingly allows to incorporate a drug within a first polymer at a high concentration and particularly above its solubility threshold in classical solvents used for drug incorporation, such as chloroform or dichloromethane. Solubility threshold is the maximum concentration for a drug to be soluble in a solvent at ambient temperature. Indeed, up to now, a drug is introduced in a polymer by use of a solvent, which impacts the final concentration of the drug within the polymer. According to the invention, it is now possible to provide a masterbatch and after that a drug delivery composition, wherein the concentration of the drug is greater than the concentration obtainable with a solvent-based process. For instance, the ratio drug/first polymer may be between 0.5 and 2.3, and notably 1. The drug may be introduced in the first polymer, during the preparation of masterbatch, under solid form (such as powder) or liquid form, when said first polymer is in partially or totally molten state.

Furthermore, according to the invention, it is possible to incorporate an aqueous composition comprising water and a water-soluble drug in the first polymer, during the preparation of masterbatch. According to the invention, the aqueous composition may be incorporated in the first polymer in totally or partially molten state, for instance during an extrusion process. This is particularly adapted for producing a drug delivery composition comprising a drug insoluble in classical solvents but soluble in water.

The masterbatch may further comprise one or several additional compounds.

In particular, the masterbatch may further comprise one or more additives. Generally speaking, the additives are used in order to enhance specific properties in the final product (e.g., a drug delivery device made with said masterbatch). For instance, the additives may be selected from the group consisting without limitation of plasticizers, coloring agents, processing aids, rheological agents, anti-static agents, anti-UV agents, toughening agents, compatibilizers, slip agents, flame retardant agents, anti-oxidants, pro-oxidants, light stabilizers, oxygen scavengers, adhesives, products, excipients, contrast agents, filler such as mineral agent such as hydroxyapatite. Advantageously, the masterbatch comprises less than 20% by weight of such additives, preferably less than 10%, more preferably less than 5%, typically between 0.1 and 4% by weight of such additives.

In a particular embodiment, the drug represents between 0.1% and 90% by weight of the masterbatch, based on the total weight of the masterbatch, preferably between 0.1% and 60%, more preferably between 0.1% and 50%, even more preferably between 0.1% and 40%. In a particular embodiment, the drug represents between 0.1% and 70%. In another particular embodiment, the drug represents between 1% and 60%, preferably between 1% and 50%.

In a particular embodiment, the masterbatch composition comprises, based on the total weight of the masterbatch:
from 10 to 99% by weight of a first polymer;
from 0.1 to 90% by weight of drug; and optionally
at least one additive.

In a particular embodiment, the masterbatch composition comprises, based on the total weight of the masterbatch:
from 10 to 99.9% by weight of a first polymer;
from 0.1 to 90% by weight of drug; and optionally
at least one additive.

In another particular embodiment, the masterbatch comprises, based on the total weight of the masterbatch:
from 30 to 99% by weight of a first polymer;
from 1 to 70% by weight of drug; and optionally
at least one additive.

In another particular embodiment, the masterbatch comprises, based on the total weight of the masterbatch:
from 40 to 99% by weight of a first polymer;
from 1 to 60% by weight of drug; and optionally
at least one additive.

In another particular embodiment, the masterbatch comprises, based on the total weight of the masterbatch:
from 50 to 99% by weight of a first polymer;
from 1 to 50% by weight of drug; and optionally
at least one additive.

In another particular embodiment, the masterbatch comprises, based on the total weight of the masterbatch, 50%+1-10% by weight of a first polymer, 50%+1-10% by weight of drug and optionally at least one additive.

In another particular embodiment, the masterbatch comprises, based on the total weight of the masterbatch:

from 90 to 99% by weight of a first polymer;
from 1 to 10% by weight of drug; and optionally
at least one additive.

In a particular embodiment, the masterbatch may further comprise a polymer-degrading enzyme. Advantageously, the polymer-degrading enzyme is able to degrade the first polymer. Alternatively, or in addition, the polymer-degrading enzyme is advantageously able to degrade at least one polymer of the final drug delivery composition or device that incorporates the masterbatch. It is also possible to introduce such polymer-degrading enzyme directly during step (b) instead of by the way of the masterbatch.

In the context of the invention, a "polymer-degrading enzyme" refers to an enzyme suitable for hydrolyzing chemical bonds between monomers of at least one polymer. Preferably, the polymer-degrading enzyme is suitable for depolymerizing at least one polymer of the drug delivery composition up to oligomers and/or monomers. Advantageously, the oligomers and/or monomers are innocuous for the human body. In a particular embodiment, the degrading enzyme is able to depolymerize the polymer of the drug delivery composition up to monomers. Such embodiment may be of particular interest for shaping medical devices that are implanted into a body, in order to favor the biological elimination of the by-products of the medical device.

Preferably, the polymer-degrading enzyme is suitable for depolymerizing at least one polyester of the drug delivery device up to oligomers and/or monomers.

In a particular embodiment, the degrading enzyme is active at 37° C. and/or at pH between 7 and 7.5. In another particular embodiment, the degrading enzyme is selected from an enzyme having an optimum pH, close to physiological pH, i.e. a pH between 6 and 8.

The degrading enzyme is preferably selected from cutinase (EC 3.1.1.74), lipase (EC 3.1.1.3), esterase, carboxylesterase (EC 3.1.1.1), serine protease (EC 3.4.21.64), protease, and oligomer hydrolase.

For example, serine protease (like Proteinase K from *Tritirachium album* or PLA depolymerase from *Amycolatopsis* sp., *Actinomadura keratinilytica, Laceyella sacchari* LP175, *Thermus* sp., or *Bacillus licheniformis* or any reformulated commercial enzymes known for degrading PLA such as Savinase®, Esperase®, Everlase® or any enzymes from the family of the subtilisin CAS 9014-01-1 or any functional variant thereof), or lipase (like the one from *Candida antarctica* or *Cryptococcus* sp or *Aspergillus niger*) or esterase (like the one from *Thermobifida halotolerans*) or variants thereof may be used for depolymerizing a drug delivery composition containing polylactic acid (PLA). A cutinase (like the one from *Thermobifida fusca* or *Thermobifida alba* or *Fusarium solani pisi*) or a lipase (like lipase PS from *Burkholderia cepacia*) or variants thereof may be used for depolymerizing a drug delivery composition containing PCL. Proteases (such as carboxypeptidase, clostridiopeptidase, alpha-chymotrypsin, trypsin or ficin) or esterases or variants thereof may be used for depolymerizing a drug delivery device containing PGA.

In a specific embodiment, the masterbatch comprises from 1 to 70% by weight of a drug and from 30 to 99% by weight of polycaprolactone, preferably from 1 to 60% by weight of a drug and from 40 to 99% by weight of polycaprolactone. In a particular embodiment, the masterbatch comprises from 40% to 60% by weight of PCL and from 40% to 60% by weight of a drug selected from proteins (such as lysozyme) or a pharmaceutical compound used to manage alcohol or opioid dependence (such as naltrexone). In another particular embodiment, the masterbatch comprises from 95% to 99% by weight of PCL and from 1% to 5% by weight of antibodies (such as monoclonal antibodies).

In a specific embodiment, the masterbatch comprises from 1 to 70% by weight of a drug and from 30 to 99% by weight of PLGA, preferably from 1 to 60% by weight of a drug and from 40 to 99% by weight of PLGA. In a particular embodiment, the masterbatch comprises from 40% to 60% by weight of PLGA and from 40% to 60% by weight of a drug selected from proteins (such as lysozyme) or a pharmaceutical compound used to manage alcohol or opioid dependence (such as naltrexone). In another particular embodiment, the masterbatch comprises from 95% to 99% by weight of PLGA and from 1% to 5% by weight of antibodies (such as monoclonal antibodies).

In another embodiment, the masterbatch comprises from 1 to 60% by weight of a drug and from 40 to 99% by weight of PLA, preferably from 1 to 40% by weight of a drug and from 60 to 99% by weight of PLA.

In a particular embodiment, the masterbatch is produced by a process called "compounding", usually an extrusion-granulation process, in which the first polymer is melted and mixed with the drug. Compounding combines mixing and blending techniques during a heat process, in order to ensure uniformity, homogeneity and dispersion in the final compound. The compounding is a technique known by a person skilled in the art. Such compounding process may be carried out with an extruder, such as single-screw extruders, multi-screw extruders of either co-rotating or counter-rotating design, dispersive kneaders, reciprocating single-screw extruder (co-kneaders).

More generally, the step (a) of preparing the masterbatch may be carried out with an extruder, wherein the first polymer is heated, melted and mixed with the drug.

In a preferred embodiment, the extruder used for the production of the masterbatch is a multi-screw extruder, preferably a twin-screw extruder, more preferably a co-rotative twin-screw extruder. In a particular embodiment, the extruder further comprises, after the screws, a static mixer. In another embodiment, the extruder is used with a die pierced with holes, preferably a two holes die.

In a preferred embodiment, the residence time of the mixture of first polymer and drug in the extruder is comprised between 5 seconds and 3 minutes, preferably is less than 2 minutes, more preferably less than 1 minute. When the masterbatch comprises a polymer with a melting temperature below 120° C., the residence time of the mixture in the extruder is preferably less than 2 minutes. One skilled in the art will easily adapt the characteristics of the extruder (e.g., the length and diameter of the strew(s), etc.), and the residence time to the first polymer, the drug and the type of masterbatch intended.

As disclosed above, the drug may be introduced in the extruder in a powder or liquid form such as a liquid formulation. In a particular embodiment, the drug is formulated within an aqueous solvent, preferably water, before to be introduced in the first polymer.

In the same way, if present, the polymer-degrading enzyme may be introduced in the extruder in a powder or liquid form, such as a liquid formulation comprising a stabilizing and/or solubilizing component (e.g., water, glycerol, sorbitol, dextrin, including maltodextrine and cyclodextrine, starch, glycol such as propanediol, salt, etc.).

In one embodiment, the drug and enzyme are incorporated simultaneously, preferably at a temperature T which is above the glass transition temperature (Tg) of the first polymer, preferably at or above the melting temperature of the first polymer.

In another embodiment, the drug and the enzyme are incorporated sequentially. For instance, the enzyme is incorporated first, preferably at a temperature T which is above the glass transition temperature (Tg) of the first polymer, preferably at or above the melting temperature of the polymer, and the drug is subsequently incorporated, preferably at a temperature T between the glass transition temperature (Tg) and the melting temperature of said first polymer.

Alternatively, the drug is incorporated first, preferably at a temperature T which is above the glass transition temperature (Tg) of the first polymer, preferably at or above the melting temperature of the first polymer, and the enzyme is subsequently incorporated, preferably at a temperature T between the glass transition temperature (Tg) and the melting temperature of said first polymer.

Advantageously, the drug and/or polymer-degrading enzyme are introduced at a late stage of the extrusion, and more particularly once the first polymer is in a partially or totally molten state. Thus, the exposure to elevated temperature is reduced. Preferably, the residence time of the drug and/or polymer-degrading enzyme in the extruder is half as long as the residence time of the first polymer, or less.

According to the invention, after step (a) of preparing the masterbatch, said masterbatch may be conditioned in any suitable solid form. In this regard, in a preferred embodiment, the masterbatch is shaped into a rod through a die. The rod is then cooled, and optionally dried before to be chopped in the form of granulates and/or pastilles of masterbatch. In a further embodiment, said granulates of masterbatch may be pulverized or micronized to produce a powder of said masterbatch. It is then possible to submit the powder to an extrusion-granulation process, preferably in an extruder so that the mixture is in a partially or totally molten state, before step (b).

Enzyme and drug can be formulated in any support known by the person skilled in the art. A single formulation containing both enzyme and drug can be used.

Polymer-Based Matrix

According to the process of the invention, the masterbatch is mixed with a polymer-based matrix in order to produce a drug delivery composition. The step of mixing the masterbatch with the polymer-based matrix is performed at a temperature at which both the first polymer and at least a polymer of the polymer-based matrix are in a partially or totally molten state.

Preferably, the polymer-based matrix comprises at least one polymer chosen among polyesters, polyethers or ester-ether copolymers.

More preferably, the polyester is selected from, polylactic acid (PLA), poly(L-lactic acid) (PLLA), poly(D-lactic acid) (PDLA), poly(D,L-lactic acid) (PDLLA), stereocomplex PLA (scPLA), polyglycolic acid (PGA), polyhydroxy alkanoate (PHA), Poly(3-hydroxybutyrate) (P(3HB)/PHB), Poly(3-hydroxyvalerate) (P(3HV)/PHV), Poly(3-hydroxyhexanoate) (P(3HHx)), Poly(3-hydroxyoctanoate) (P(3H0)), Poly(3-hydroxydécanoate) (P(3HD)), Poly(3-hydroxybutyrate-co-3-hydroxyvalerate) (P(3HB-co-3HV)/PHBV), Poly(3-hydroxybutyrate-co-3-hydroxyhexanoate) (P(3HB-co-3HHx)/ (PHBHHx)), Poly(3-hydroxybutyrate-co-5-hydroxyvalerate) (PHB 5HV), Poly(3-hydroxybutyrate-co-3-hydroxypropionate) (PHB3HP), Polyhydroxybutyrate-co-hydroxyoctonoate (PHBO), polyhydroxybutyrate-co-hydroxyoctadecanoate (PHB Od), Poly(3-hydroxybutyrate-co-3-hydroxyvalerate-co-4-hydroxybutyrate) (P(3HB-co-3HV-co-4HB)), polybutylene succinate (PBS), polybutylen succinate adipate (PBSA), polybutylen adipate terephthalate (PBAT), polycaprolactone (PCL), poly(ethylene adipate) (PEA) and copolymers thereof such as poly(lactic-co-glycolic acid) copolymers (PLGA) or blends/mixtures of these materials. The polyethers may be selected e.g., from polyethylene glycol (PEG), preferably PEG with molecular mass above 600 g/mol, polyethylene oxide (PEO), or copolymers and blends/mixtures thereof. The ester-ether copolymers may be selected e.g., from polydioxanone (PDS).

In a particular embodiment, the polymer-based matrix comprises at least one polymer selected from polylactic acid (PLA), polybutylene adipate terephthalate (PBAT), polyhydroxyalkanoate (PHA), polyglycolic acid (PGA), polybutylene succinate (PBS), polycaprolactone (PCL), poly(ethylene adipate) (PEA), dextrane, gelatin, poly butylene succinate adipate (PBSA), polybutylene adipate terephthalate (PBAT), polydioxanone (PDS), polyhdroxyalkanoate (PHA), polyethylene glycol (PEG), preferably PEG with molecular mass above 600 g/mol, polyethylene oxide (PEO) or copolymers thereof such as poly(lactic-co-glycolic acid) copolymers (PLGA or PLA-co-PGA), and blends/mixtures thereof.

In a particular embodiment, the polymer-based matrix comprises PLA. Such polymer-based matrix may further comprise at least one additional polymer, preferably selected from polybutylene adipate terephthalate (PBAT), polyhydroxyalkanoate (PHA), polyglycolic acid (PGA), polybutylene succinate (PBS), polycaprolactone (PCL), poly(ethylene adipate) (PEA), dextrane, gelatin, and blends/mixtures thereof. Alternatively, the polymer-based matrix contains PLA as the only polymer, preferably PLLA and/or PDLA.

In an embodiment, the polymer-based matrix comprises lactic acid copolymers, preferably selected from PLA-based heteropolymers, more preferably selected from poly(lactic-co-glycolic acid) copolymers (PLA-co-PGA or PLGA), poly(lactic-co-caprolactone) copolymers (PLA-co-PCL), poly(lactic-co-ethyleneglycol) copolymers (PLA-co-PEG), poly(lactic-co-ethylene oxide) copolymers (PLA-co-PEO) or grafted PLA (PLA-g-gelatine). In a particular embodiment, the polymer-based matrix comprises copolymers of PLA and PGA (PLGA or PLA-co-PGA).

In another particular embodiment, the polymer-based matrix contains PCL. Such polymer-based matrix may further comprise at least one additional polymer, preferably selected from polybutylene adipate terephthalate (PBAT), polyhydroxyalkanoate (PHA), polyglycolic acid (PGA), polybutylene succinate (PBS), polylactic acid (PLA), poly(ethylene adipate) (PEA), dextrane, gelatin, starch cellulose and its derivatives and blends/mixtures of these polyesters or copolymers. Alternatively, the polymer-based matrix contains PCL as the only polymer.

In a particular embodiment, the polymer-based matrix comprises at least one polymer selected from polymers that are naturally degradable under physiological conditions, i.e. that degrades at least partially into monomers and/or oligomers under physiological conditions in less than 5 years, preferably less than 2 years.

One skilled in the art is able to choose the polymer(s) of the polymer-based matrix depending on the nature of the drug delivery composition. For use for shaping a medical device that must be implanted into a mammal body, the polymers of the polymer-based matrix must be chosen among the polymers that innocuously disintegrate or break down as safe unit structures. Furthermore, the choice of the polymer can also be driven by the intended use of the medical device. Indeed, in case of medical devices that must be implanted into a body, it is important to take into account the molecular mass of the unit structures that are acceptable to allow their biological elimination (e.g., renal elimination, hepatic elimination, etc.).

According to the invention, the polymer-based matrix may further contain additives such as acid neutralizing agents, preferably selected from carbonate salts, calcium phosphate, hydrotalcite, talc, mica, and clay.

Process for Preparing the Drug Delivery Composition

It is the purpose of the invention to provide a process wherein a polymer-based matrix is mixed with a masterbatch that comprises a high amount of a drug to realize a drug delivery composition in which the drug is precisely added and homogeneously distributed.

Such homogeneity of the distribution in the polymer-based matrix leads to a final drug-delivery composition, and thereby of a drug-delivery device made with this composition, that presents a homogenous reparation of the drug. Such homogeneous distribution may be obtained e.g., by heating the polymer-based matrix until it is at least partially molten to allow incorporation into the molten composition of the drug and/or the enzyme. The final drug delivery composition is advantageously in a solid state. However, it is possible to provide a drug-delivery composition that is in a molten or even liquid state.

According to the invention, step (b) of mixing the masterbatch with the polymer-based matrix is performed at a temperature at which at least one polymer of the polymer-based matrix is in a partially or totally molten state. With regard to amorphous polymers, a totally or partially molten state corresponds to a rubbery or softened state, i.e. a state at which such polymers are fluid enough to be processed by extrusion. Preferably, if the polymer-based matrix comprises more than one polymer, step (b) is performed at a temperature at which all the polymers are in a partially or totally molten state.

The polymer-based matrix may be at least partially melted during a heat treatment to allow the incorporation into the melted matrix of the masterbatch. Advantageously, the heat treatment is performed at a temperature at which both the polymer-based matrix and the masterbatch are in a partially or totally molten state.

In a particular embodiment, step (b) is performed at a temperature T between 50° C. and 200° C., preferably between 60° C. and 180° C., more preferably between 70° C. and 160° C. The temperature T can be adapted by a person skilled in the art depending on the polymer of the polymer-based matrix of drug delivery device.

In a particular embodiment, the masterbatch is introduced in the polymer-based matrix at a temperature T between the glass transition temperature (Tg) and the melting temperature of at least one polymer of the polymer-based matrix.

In another particular embodiment, the masterbatch is introduced in the polymer-based matrix at a temperature T which is above the glass transition temperature (Tg) of at least one polymer of the polymer-based matrix, preferably at or above the melting temperature of said polymer.

In a particular embodiment, a polymer-degrading enzyme is also introduced into the polymer-based matrix during step (b). Preferably, the polymer-degrading enzyme is able to degrade at least one polymer of the polymer-based matrix.

In one embodiment, the masterbatch and enzyme are incorporated simultaneously, preferably at a temperature T which is above the glass transition temperature (Tg) of the polymer, preferably at or above the melting temperature of the polymer of the polymer-based matrix.

In another embodiment, the masterbatch and the enzyme are incorporated sequentially. For instance, the enzyme is incorporated first, preferably at a temperature T which is above the glass transition temperature (Tg) of the polymer of the polymer-based matrix, preferably at or above the melting temperature of the polymer, and the masterbatch is subsequently incorporated, preferably at a temperature T between the glass transition temperature (Tg) and the melting temperature of said polymer. Alternatively, the masterbatch is incorporated first, preferably at a temperature T which is above the glass transition temperature (Tg) of the polymer, preferably at or above the melting temperature of the polymer of the polymer-based matrix, and the enzyme is subsequently incorporated, preferably at a temperature T between the glass transition temperature (Tg) and the melting temperature of said polymer.

Advantageously, step (b) is implemented during a heat treatment, wherein at least the polymer-based matrix is in partially or totally molten state.

In a particular embodiment, step (b) is performed by extrusion, internal mixing, co-kneading, extrusion-compounding, extrusion blow-molding, cast film extrusion, calendaring, thermoforming, injection-molding, compression molding, extrusion-swelling, rotary molding, ironing, coating, stratification, expansion, pultrusion, compression-granulation and 3D printing such as fused deposition modelling, selective laser sintering or binder jetting.

In a preferred embodiment, the residence time of the polymer-based matrix in the extruder is comprised between 5 seconds and 3 minutes, preferably is less than 2 minutes, more preferably less than 1 minute. When the polymer-based matrix comprises a polymer with a melting temperature below 120° C., the residence time of the mixture in the extruder is preferably less than 2 minutes. One skilled in the art will easily adapt the characteristics of the extruder (e.g., the length and diameter of the strew(s), etc.), and the residence time to the polymer-based matrix, the masterbatch and the type of drug delivery composition intended.

Advantageously, the masterbatch and/or the polymer-degrading enzyme are introduced at a late stage of the heat treatment, and more particularly once the polymer-based matrix is in a partially or totally molten state. Thus, the exposure to elevated temperature is reduced. Preferably, the residence time of the masterbatch and/or polymer-degrading enzyme in the extruder is half as long as the residence time of the polymer-based matrix, or less.

Drug Delivery Composition

It is the purpose of the invention to provide new drug delivery compositions allowing release, preferably in a controlled rate, of a drug that is incorporated into said delivery composition.

In a particular embodiment, the drug delivery composition is a pharmaceutical composition. Such pharmaceutical composition may be in the form of a tablet, gel, coating, particles, or microbeads.

It is also a purpose of the invention to provide a new drug delivery device allowing to release, preferably in a controlled rate, a drug that is included into said delivery device. Accordingly, the composition of the invention may advantageously be used to shape a drug delivery device, more particularly a medical device.

Such medical device may be in the form of an implant, film, stent, leaflet, valve, coil, scaffold, dressing, rod, patch, fibers, suture fibers, screw, bone plate or implant, bone cement and prostheses.

In a particular embodiment, the drug delivery composition comprises from 51 to 99.999% by weight of polymer-based matrix,
from 0.001 to 49% by weight of a drug, and
from 0.001 to 30% by weight of the polymer-degrading enzyme.

In a particular embodiment, the drug delivery composition comprises
from 50 to 99.998% by weight of polymer-based matrix,
from 0.001 to 49.99% by weight of a drug, and
from 0.001 to 30% by weight of the polymer-degrading enzyme.

In a preferred embodiment, the drug delivery composition comprises
from 60 to 99.98% by weight of polymer-based matrix,
from 0.01 to 39% by weight of a drug, and
from 0.01 to 20% by weight of the polymer-degrading enzyme.

In a particular embodiment, a masterbatch comprising PCL and a drug, is diluted in a polymer-based matrix of PLA. In another particular embodiment, a masterbatch comprising PCL and a drug, is diluted in a polymer-based matrix of PLGA. In another particular embodiment, a masterbatch comprising PCL and a drug, is diluted in a polymer-based matrix of PGA.

In a particular embodiment, a masterbatch comprising PCL and a drug selected from bone regenerative enzymes, anti-inflammatory agents (e.g., ibuprofene), analgesic (e.g., paracetamol, morphine), anti-diabetics (e.g., insulin), hormone (e.g., progesterone), cytokine, monoclonal antibody, antigen, contraceptive agent, anti-tumor agent, and anti-infectious agent are diluted in a polymer-based matrix of PLA.

In another particular embodiment, a masterbatch comprising PCL and a drug selected from bone regenerative enzymes, anti-inflammatory agents (e.g., ibuprofene), analgesic (e.g., paracetamol, morphine), anti-diabetics (e.g., insulin), hormone (e.g., progesterone), cytokine, monoclonal antibody, antigen, contraceptive agent, anti-tumor agent, and anti-infectious agent are diluted in a polymer-based matrix of PCL.

In another particular embodiment, a masterbatch comprising PCL and a drug selected from bone regenerative enzymes, anti-inflammatory agents (e.g., ibuprofene), analgesic (e.g., paracetamol, morphine), anti-diabetics (e.g., insulin), hormone (e.g., progesterone), cytokine, monoclonal antibody, antigen, contraceptive agent, anti-tumor agent, and anti-infectious agent are diluted in a polymer-based matrix of PCL/PLA.

In another particular embodiment, a masterbatch comprising PCL and a drug selected from bone regenerative enzymes, anti-inflammatory agents (e.g., ibuprofene), analgesic (e.g., paracetamol, morphine), anti-diabetics (e.g., insulin), hormone (e.g., progesterone), cytokine, monoclonal antibody, antigen, contraceptive agent, anti-tumor agent, and anti-infectious agent are diluted in a polymer-based matrix of PGA.

In another particular embodiment, a masterbatch comprising PCL and a drug selected from bone regenerative enzymes, anti-inflammatory agents (e.g., ibuprofene), analgesic (e.g., paracetamol, morphine), anti-diabetics (e.g., insulin), hormone (e.g., progesterone), cytokine, monoclonal antibody, antigen, contraceptive agent, anti-tumor agent, and anti-infectious agent are diluted in a polymer-based matrix of PGA/PCL.

In another particular embodiment, a masterbatch comprising PLGA and a drug, is diluted in a polymer-based matrix of PLA. In another particular embodiment, a masterbatch comprising PLGA and a drug, is diluted in a polymer-based matrix of PLGA. In another particular embodiment, a masterbatch comprising PLGA and a drug, is diluted in a polymer-based matrix of PGA.

In another particular embodiment, a masterbatch comprising PLGA and a drug selected from proteins (such as lysozyme), a pharmaceutical compound used to manage alcohol or opioid dependence (such as naltrexone) are diluted in a polymer-based matrix of PLGA.

In another particular embodiment, a masterbatch comprising PCL and a drug selected from proteins (such as lysozyme) or antibodies (such as monoclonal antibodies) are diluted in a polymer-based matrix of PLGA.

In another particular embodiment, a masterbatch comprising PCL and a drug selected from proteins (such as lysozyme) are diluted in a polymer-based matrix of PLA.

In another particular embodiment, a masterbatch comprising PCL, a drug selected from proteins (such as lysozyme) and a PLA-degrading enzyme are diluted in a polymer-based matrix of PLA.

The use of a masterbatch as a tool for introducing a drug into the final drug-delivery composition (and thereby into the final drug-delivery device) allows to control with more accuracy the final dosage of the drug into the drug-delivery composition/device. Furthermore, the drug is distributed more homogeneously compared to drug-delivery compositions/devices prepared with other processes.

In a particular embodiment, the drug delivery composition is a pharmaceutical composition. Such pharmaceutical composition may be in the form of a tablet, gel, coating, particles, or microbeads.

In a particular embodiment, the drug-delivery composition is shaped to form a drug-delivery device, more particularly a medical device. Such medical device may be in the form of an implant, film, stent, leaflet, valve, coil, scaffold, dressing, rod, patch, fibers, suture fibers, screw, bone plate or implant, bone cement and prostheses.

EXAMPLES

Example 1—Drug Delivery Composition Comprising PLGA Copolymer and Naltrexone Produced by the Process of the Invention from a PLGA Co-Polymer Masterbatch A masterbatch comprising 50% PLGA copolymer and 50% naltrexone hydrochloride was prepared by mixing polylactic acid and polyglycolic acid copolymer (PLGA-PURASORB PDLG 5002A from Corbion Purac which is in a partially or totally molten state at a temperature above 90° C.-100° C.) and naltrexone hydrochloride powder (from Sigma-Aldrich). The mix was then extruded using a twin-screw extruder (Thermo Scientific HAAKE Minilab II) at 99° C., 80 Rpm.

A drug delivery composition was prepared by mixing the masterbatch cut in small fragments with the same copolymer of PLGA (PURASORB PDLG 5002A from Corbion Purac) in different proportions. The mixes of the drug delivery compositions were then extruded at 100° C., 80 rpm, using the same extruder as described above.

Weight of each of the component (in grams) of the drug delivery compositions are summarized in Table 1.

TABLE 1

Composition in the drug delivery compositions comprising naltrexone.

| Drug delivery composition comprising: | 5% naltrexone | 10% naltrexone |
|---|---|---|
| PLGA | 4.5 g | 4 g |
| Masterbatch (PLGA + 50% naltrexone hydrochloride) | 0.5 g | 1 g |

The degradation of the compositions obtained through the degradation of PLGA copolymer and release of naltrexone was analyzed.

About 50 mg (in one piece) of each composition was incubated at 37° C., 100 Rpm in 20 mL of potassium phosphate buffer 0.1 M pH 7.4 during several days. For each sampling point, 0.25 mL was taken off to titrate lactic acid and glycolic acid release, and naltrexone release.

The degradation of PLGA and the release of naltrexone were studied by UHPLC by titration of lactic acid and glycolic acid and naltrexone according to methods described below.

UHPLC Method Used for Lactic Acid and Glycolic Acid Titration:

An Ultimate 3000 HPLC system (Thermofisher Scientific) equipped with a Refractive Index Detector Shodex RI-101 Analytical and a Biorad Aminex HPX-87H column 300×7.8 mm 9 µm column were used. The column was controlled to a temperature of 60° C. The mobile phase was $H_2SO_4$ 5 mM with of flow rate of 0.5 mL/min. Lactic acid (LA) and glycolic acid (GA) powder was accurately weighed and dissolved in water to give 5 g/L solution of each molecule.

Subsequent dilutions were made with water to get concentrations of 0.035-2.5 g/L of LA and GA. The standard solutions prepared as above were injected (20 µL) in the same conditions of samples. The peak areas of the LA and GA concentrations were calculated. The regression of the LA and GA concentration over the peak areas was obtained and used to estimate the amount of LA and GA liberated from the polymer.

UHPLC Method Used for Naltrexone Titration:

An Ultimate 3000 HPLC system (Thermofisher Scientific) equipped with Diode Array Detector (DAD- 3000(RS)) and a Phenomenex Kinetex EVO C18, LC Column 100×2.1 mm, 2.6 µm with a pore size of 100 Å. The column was controlled to a temperature of 30° C. The mobile phase was a gradient of Ammonium Bicarbonate 20 mM pH9/Acetonitrile (95/5% to 35/65 in 5 min) with a flow rate of 0.75 mL/min. Naltrexone hydrochloride powder was accurately weighed and dissolved in water to give 450 µg/mL solution. Subsequent dilutions were made with water to get concentrations of 7-450 µg/mL. The standard solutions prepared as above were injected in the same conditions of samples. The peak areas of the naltrexone concentration were calculated. The regression of the naltrexone concentration over the peak areas was obtained and used to estimate the amount of naltrexone liberated from the polymer. HPLC profile of the naltrexone released is similar to the HPLC profile of the non-extruded molecule.

The results are shown in FIG. 1. PLGA co-polymer degradation is indicated in percentage (%) of the total lactic acid and glycolic acid present in the PLGA co-polymer of the composition and naltrexone release is indicated in percentage (%) based on the total % naltrexone embedded in the composition.

The results show that the release of naltrexone at different concentrations (5% and 10%) follows the hydrolysis of the polymer and that naltrexone has not been degraded in the masterbatch and in the drug delivery composition, since HPLC profile of naltrexone released is similar to non-extruded molecule (data not shown).

Example 2—Drug Delivery Composition Comprising PLGA Copolymer and Lysozyme Produced by the Process of the Invention from a PCL Masterbatch A masterbatch comprising 50% PCL and 50% lysozyme was prepared by mixing PCL powder (Capa™ 6500 from Perstorp, melting temperature of 58-60° C.) and lysozyme powder (from Sigma-Aldrich, melting temperature of 76° C.). The mix was then extruded using a twin-screw extruder (Thermo Scientific HAAKE Minilab II) at 78° C., 80 rpm.

A drug delivery composition comprising 10% of lysozyme was prepared by mixing 1 gram of said masterbatch cut in small fragments with 4 grams of copolymer of poly-lactic acid and poly-glycolic acid (PLGA-PURASORB PDLG5002A from Corbion Purac which is in a partially or totally molten state at a temperature above 90° C.-100° C.). A control was prepared by mixing 4 grams of PLGA with 0.5 gram of micronized PCL and 0.5 gram of lysozyme. Both mixes were then extruded at 95° C., 80 rpm using the same extruder as described above.

A non-aqueous extraction (Korber M, Bodmeier R. Development of an in situ forming PLGA drug delivery system I. Characterization of a non-aqueous protein precipitation. Eur J PharmSci. 2008 Nov. 15; 35(4):283-92) was applied to the drug delivery composition and the control followed by the lysozyme titration using the lysozyme activity kit (from Sigma-Aldrich). The results shown a greater lysozyme activity in the drug delivery composition obtained with the process of the invention (using a masterbatch) than in the control. More particularly, the lysozyme activity in the drug delivery composition was 38% higher than the lysozyme activity in the control.

The degradation of PLGA copolymer and the release of lysozyme of the drug delivery composition produced according to the invention were then analyzed using methods described below.

About 50 mg (in one piece) of the composition was incubated at 37° C., 100 Rpm in 20 mL of potassium phosphate buffer 0.1 M pH 7.4 during several days. After 12 days, 0.25 mL was taken off to titrate lactic acid and glycolic acid release and lysozyme activity.

The degradation of PLGA copolymer was analyzed by UHPLC by titration of lactic acid and glycolic acid using method described in Example 1. The release of lysozyme was analyzed by measuring its activity using the Lysozyme activity kit (from Sigma-Aldrich).

After 12 days of incubation, 21% of PLGA copolymer is degraded and 18% of lysozyme activity is measured corresponding to an estimated release of 18% of lysozyme. PLGA copolymer degradation is indicated in percentage (%) of the total lactic acid and glycolic acid present in the PLA/PGA copolymer of the composition and lysozyme release is based on the lysozyme activity released compared to the total % of activity of lysozyme embedded in the composition.

This result shows that lysozyme retains activity after two successive extrusions and that it is released from the drug delivery composition.

Example 3—Drug Delivery Composition Comprising Lysozyme and PLA Produced by the Process of the Invention from a PCL Masterbatch A masterbatch comprising 50% lysozyme and 50% PCL was prepared by mixing 2.5 g of micronized polycaprolactone (Capa™ 6500 from Perstorp) and 2.5 g of lysozyme powder (from Sigma-Aldrich). The mix was then extruded using a twin-screw extruder (Thermo Scientific HAAKE Minilab II) at 78° C., 80 Rpm with a manual loading.

A drug delivery composition of the invention comprising 10% of lysozyme was prepared by mixing 1 gram of said masterbatch cut in small fragments (around 2 mm×2 mm), with 4 grams of micronized polymer of polylactic acid (Ingeo™ Biopolymer 4043D from NatureWorks). The mix of the drug delivery composition was then extruded at 165° C. using the same extruder as described above. The twin screw extruder was used at 80 rpm with a manual loading of the composition.

The lysozyme was extracted from the masterbatch and from the drug delivery composition by liquid-liquid extraction. 50 mg of drug delivery composition were solubilized in 2.5 mL of Dichloromethane. Then 7.5 mL of cold 66 mM potassium phosphate buffer pH 6.24 was added. The mix was vigorously vortex. After phase separation, aqueous phase was taken off and lysozyme activity was measured using Lysozyme activity Kit (from Sigma-Aldrich).

The analysis indicated that about 95% of lysozyme activity is maintained in the masterbatch after one extrusion at 78° C. and that about 50% of lysozyme activity is maintained in the drug delivery composition after two extrusions at 78° C. and 165° C., based on 100% of activity of the lysozyme embedded in the composition. Thanks to the process of invention using a masterbatch, a drug with a low denaturation temperature (76° C.) can be incorporated in a high polymer-based matrix such as high molecular weight PLA, while maintaining a drug activity.

In another embodiment, a drug delivery composition of the invention comprising 10% of lysozyme and 10% of PLA-degrading enzyme was prepared by mixing 1 gram of said masterbatch cut in small fragments (around 2 mm×2 mm), 3.5 grams of micronized polymer of polylactic acid (Ingeo™ Biopolymer 4043D from NatureWorks), with 0.5 gram of powder of Savinase®, able to degrade PLA.

The formulation of Savinase® under a powder form was obtained as follow: a liquid formulation was obtained by ultrafiltration and diafiltration of the commercial Savinase® 16L (diafiltration factor about 100) on 3.5 Kd membrane to obtain a concentrated liquid composition and to remove some polyols present in the commercial solution. Arabic gum (INSTANT GUM AA—NEXIRA) was added and the composition obtained was then dried by freeze drying in order to obtain a solid composition comprising about 33% by weight of enzyme, 15.7% by weight of arabic gum, 0.5% by weight of water and 50.8% by weight of polyols (glycerol, propylene glycol) and other additives, based on the total weight of the solid composition.

The mix of the drug delivery composition was then extruded using the same extruder at 165° C., 80 rpm with a manual loading of the composition.

The lysozyme was extracted with the method explained above and after two extrusions, at 78° C. and then at 165° C., the lysozyme embedded in the composition still exhibits activity (results not shown). Thanks to the invention, a drug with a low denaturation temperature (76° C.) can be incorporated in a high melting temperature polymer such as high molecular weight PLA, while maintaining a drug activity.

Example 4—Drug Delivery Composition of the Invention Comprising PLGA Copolymer and Lysozyme Produced by the Process of the Invention from a PLGA Masterbatch A masterbatch was prepared by mixing PLGA copolymer (PURASORB PDLG 5002A from Corbion purac which is in a partially or totally molten state at a temperature above 90° C.-100° C.) and lysozyme powder (from Sigma-Aldrich). The mix was then extruded using a twin-screw extruder (Thermo Scientific HAAKE Minilab II) at 100° C., 80 rpm.

A drug delivery composition of the invention comprising 10% of lysozyme was prepared by mixing 1 gram of said masterbatch cut in small fragments with 4 grams of same co-polymer of polylactic acid and polyglycolic acid (PURASORB PDLG 5002A from Corbion purac).

The mix of the drug delivery composition was extruded using the same extruder at 100° C., 80 rpm.

About 50 mg (in one piece) of the composition were incubated at 37° C., 100 rpm in 20 mL of potassium phosphate buffer 0.1 M pH 7.4 during several days. For each sampling point, 0.25 mL was taken off to titrate lactic acid and glycolic acid release, and lysozyme release.

The degradation of PLGA was studied by UHPLC by titration of lactic acid and glycolic acid and the release of lysozyme by titration of lysozyme activity as described in Example 2.

Figure 2:
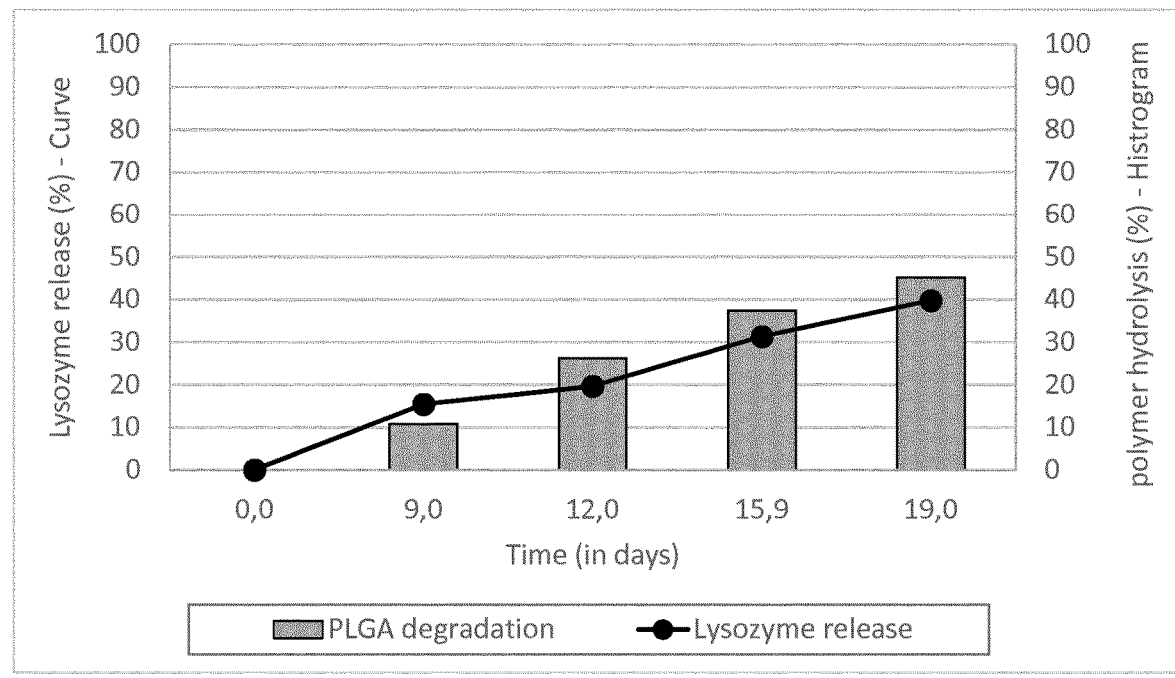
FIG. 2: PLGA degradation and lysozyme activity release of a drug delivery composition produced by the process of the invention comprising PLGA and 10% lysozyme.

The results are shown in FIG. 2. PLGA copolymer degradation is indicated in percentage (%) of the total lactic acid and glycolic acid present in the PLGA copolymer of the composition and lysozyme release is based on the lysozyme activity released and is indicated in % of the total lysozyme activity embedded in the composition.

This result shows that lysozyme retains activity after two successive extrusions and that the lysozyme release is correlated with polymer hydrolysis.

According to another embodiment, another drug delivery composition of the invention comprising 10% of lysozyme was prepared by mixing 1 gram of said masterbatch, with 4 grams of another PLGA copolymer (PURASORB PDLG 5010 from Corbion Purac).

The mix of the drug delivery composition was extruded using the same extruder at 100° C., 80 rpm.

The degradation of the composition obtained through the degradation of PLGA co-polymer and the release of lysozyme by titration of lysozyme activity were analyzed as described in Example 2.

After 21 days, the PLGA copolymer show about 5% of degradation and lysozyme activity release is evaluated at 10%, wherein PLGA copolymer degradation is indicated in percentage (%) of the total lactic acid and glycolic acid present in the PLGA of the composition and lysozyme release is based on the lysozyme activity released and is indicated in % of the total lysozyme activity embedded in the composition.

This result shows that lysozyme retains activity after two successive extrusions and is released when included in a drug delivery device put under physiological conditions.

Example 5—Drug Delivery Composition of the Invention Comprising PLGA and Monoclonal Antibody Produced by the Process of the Invention from a PCL Masterbatch A masterbatch comprising 96.8% PCL and 3.2% monoclonal antibodies Adalimumab was prepared by mixing PCL powder (Capa™ 6500 from Perstorp, melting temperature of 58-60° C.) and Adalimumab (Humira®, molecular weight about 148 kDa and a denaturation temperature about 75° C.) which was beforehand lyophilized using a laboratory lyophiliser (CHRIST LSC alpha 2-4). The mix was then extruded using a twin-screw extruder (Thermo Scientific HAAKE Minilab II) at 70° C., 80 Rpm.

A drug delivery composition of the invention comprising 0.8% of antibody was prepared by mixing 1.25 gram of said masterbatch cut in small fragments with 4.8 grams (79%) of PLGA (PURASORB PDLG5002A from Corbion Purac). The mix was then extruded using the same extruder as described above at 90° C., 80 rpm.

A nonaqueous extraction (Korber M, Bodmeier R. Development of an in situ forming PLGA drug delivery system I. Characterization of a non-aqueous protein precipitation. Eur J PharmSci. 2008 Nov. 15; 35(4):283-92) was applied to the drug delivery composition followed by a Adalimumab titration using the Kit Lisa Tracker Adalimumab (from Theradiag). This shows that 42% of Adalimumab remained functional in the drug delivery composition, after the 2 extrusions at 70° C. and at 90° C.

Release of Adalimumab of the drug delivery composition was also studied through the evaluation of the activity of the antibodies released. About 50 mg (in one piece) of each composition were incubated at 37° C., 100 Rpm in 20 mL of potassium phosphate buffer 0.1 M pH 7.4 during several days. For each sampling point, 0.5 mL was taken off to titrate Adalimumab activity by ELISA using the Kit Lisa Tracker Adalimumab (from Theradiag).

After 7 days the antibody activity was evaluated at 11%, based on the total % of active antibody in the composition after extrusion, estimating thus that 11% of the antibodies were released after 7 days.

Monoclonal antibody retains activity after two successive extrusions and is released when included in a drug delivery device put under physiological conditions.

The invention claimed is:

1. A process for preparing a drug delivery composition comprising at least a drug, comprising the steps of
    a) preparing a masterbatch comprising a drug and a first polymer by
        (i) heating the first polymer, wherein said first polymer has a melting temperature below 140° C.; and
        (ii) introducing the drug during heating of the first polymer, with a drug content between 0.1% and 90%, based on the total weight of the masterbatch; and
    b) introducing the masterbatch in a polymer-based matrix during production of the drug delivery composition,
    wherein step a) is performed at a temperature at which the first polymer is in a partially or totally molten state, and step b) is performed at a temperature at which both the first polymer and at least a polymer of the polymer-based matrix are in a partially or totally molten state,
    wherein the drug is selected from bone regenerative enzymes, hormones, cytokines, monoclonal antibodies and antigens;
    and wherein the drug has a molecular mass above 14 kDa.

2. The process of claim 1, wherein the drug is deprived of any polymer-degrading activity.

3. The process of claim 1, wherein the drug is selected from proteins selected from bone regenerative enzymes, antibodies and hormones.

4. The process of claim 1, wherein the drug represents between 0.1% and 80%, based on the total weight of the masterbatch.

5. The process of claim 1, wherein the drug represents between 0.01 and 49% by weight of the drug delivery composition, based on the total weight of the drug delivery composition.

6. The process of claim 1, wherein the first polymer is a polyester and/or polyether.

7. The process of claim 1, wherein the first polymer is a polyester selected from polycaprolactone (PCL), poly butylene succinate adipate (PBSA), polybutylene adipate terephthalate (PBAT), polyhdroxyalkanoate (PHA), polylactic acid (PLA), polyglycolic acid (PGA) and copolymers.

8. The process of claim 1, wherein step b) is performed at a temperature T between 50° C. and 200° C.

9. The process of claim 1, wherein step b) is performed by extrusion, internal mixing, co-kneading, extrusion-compounding, extrusion blow-molding, cast film extrusion, calendaring, thermoforming, injection-molding, compression molding, extrusion-swelling, rotary molding, ironing, coating, stratification, expansion, pultrusion, compression-granulation and 3D printing.

10. The process of claim 1, wherein the masterbatch is introduced in the polymer-based matrix at a temperature T between the glass transition temperature (Tg) and the melting temperature of at least one polymer of the polymer-based matrix.

11. The process of claim 1, wherein the masterbatch is introduced in the polymer-based matrix at a temperature T which is above the glass transition temperature (Tg) of at least one polymer of the polymer-based matrix.

12. The process of claim 1, wherein the polymer-based matrix comprises a polyester, selected from PLA, PCL, polybutylene adipate terephthalate (PBAT), polyhydroxyalkanoate (PHA), polyglycolic acid (PGA), polybutylene succinate (PBS), poly(ethylene adipate) (PEA), and copolymers or blends/mixtures thereof.

13. The process of claim 1, wherein the polymer-based matrix contains PLLA and/or PDLA.

14. The process of claim 13, wherein PLLA and/or PDLA are the only polymers of the polymer-based matrix.

15. The process of claim 1, wherein the polymer-based matrix contains copolymer PLGA.

16. The process of claim 15, wherein copolymer PLGA is the only polymer of the polymer-based matrix.

17. The process of claim 1, wherein the drug delivery composition further contains a polymer-degrading enzyme suitable for degrading at least one polymer of the polymer-based matrix.

18. The process of claim 17, wherein the polymer-degrading enzyme is selected from proteases, esterase, cutinases, and lipases.

19. The process of claim 17, wherein the polymer-degrading enzyme is introduced in the masterbatch during step a).

20. The process of claim 17, wherein the polymer-degrading enzyme is introduced in the polymer-based matrix during step b).

21. The process of claim 1, wherein the drug delivery composition is a pharmaceutical composition, selected from tablet, gel, coating, particles and microbeads.

22. The process of claim 1, wherein the drug delivery composition is shaped to form a drug delivery device, selected from implant, film, stent, leaflet, valve, coil, scaffold, dressing, rod, patch, fibers, suture fibers, screw, bone plate or implant, bone cement, and prostheses.

23. The process of claim 1, wherein the drug has a molecular mass above 20 kDa.

* * * * *